US008888675B2

(12) United States Patent
Stankus et al.

(10) Patent No.: US 8,888,675 B2
(45) Date of Patent: Nov. 18, 2014

(54) APPARATUS AND METHODS FOR SUPPORTING CARDIAC ISCHEMIC TISSUE

(75) Inventors: John J. Stankus, Campbell, CA (US); Barbara E. Stamberg, San Jose, CA (US); Pamela A. Kramer-Brown, San Jose, CA (US); Jesus Magana, Redwood City, CA (US); Shubhayu Basu, Solon, OH (US); Yuet Mei Khong, Sunnyvale, CA (US); Florian N. Ludwig, Ebikon (CH)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 522 days.

(21) Appl. No.: 12/855,469

(22) Filed: Aug. 12, 2010

(65) Prior Publication Data

US 2012/0041257 A1 Feb. 16, 2012

(51) Int. Cl.
*A61F 2/00* (2006.01)
*A61N 1/362* (2006.01)
*A61B 17/12* (2006.01)
*A61B 17/064* (2006.01)
*A61F 2/24* (2006.01)
*A61B 17/068* (2006.01)

(52) U.S. Cl.
CPC ......... *A61F 2/2487* (2013.01); *A61B 17/12186* (2013.01); *A61B 17/064* (2013.01); *A61L 2430/20* (2013.01); *A61B 17/12195* (2013.01); *A61B 17/12122* (2013.01); *A61B 17/12181* (2013.01); *A61B 2017/0647* (2013.01); *A61B 17/068* (2013.01)

USPC .............................................. 600/16; 600/37

(58) Field of Classification Search
USPC ....................................... 600/37, 16–1, 378
See application file for complete search history.

(56) References Cited

U.S. PATENT DOCUMENTS 6,450,171 B1 * 9/2002 Buckberg et al. ............. 128/898
7,399,271 B2 * 7/2008 Khairkhahan et al. .......... 600/16

(Continued)

FOREIGN PATENT DOCUMENTS

WO WO 2012/021513 2/2012

OTHER PUBLICATIONS

"Break," in Dictionary.com Unabridged. Source location: Random House, Inc. http://dictionary.reference.com/browse/breaking. Available: http://dictionary.reference.com. Accessed: Jun. 6, 2013.*

*Primary Examiner* — Jacqueline Cheng
*Assistant Examiner* — Kaylee Wilson
(74) *Attorney, Agent, or Firm* — Workman Nydegger; Jonathan D. Feuchtwang

(57) ABSTRACT

Apparatus and methods are disclosed for supporting ischemic tissue of the heart using scaffolds that may be placed within the heart percutaneously. A scaffold assembly may include a layer of biocompatible material detachably secured to a placement rod, such that the placement rod may be used to urge the layer of biocompatible material through a catheter to adjacent an area of ischemic tissue. Anchors may secure the layer of material to the myocardium. Multiple layers of biocompatible material may be placed in the ventricle separately to form the scaffold. In some embodiments, a scaffold is formed or reinforced by injecting a polymer, such as a viscoelastic foam, around an inflatable member inflated within a ventricle.

31 Claims, 16 Drawing Sheets

(56) References Cited

U.S. PATENT DOCUMENTS

| | | | |
|---|---|---|---|
| 2004/0158123 A1* | 8/2004 | Jayaraman | 600/37 |
| 2005/0096498 A1* | 5/2005 | Houser et al. | 600/37 |
| 2005/0154252 A1 | 7/2005 | Sharkey et al. | |
| 2006/0264980 A1* | 11/2006 | Khairkhahan et al. | 606/153 |
| 2006/0293739 A1* | 12/2006 | Vijay | 607/122 |
| 2008/0045778 A1 | 2/2008 | Lichtenstein et al. | |
| 2008/0097560 A1* | 4/2008 | Radziunas et al. | 607/104 |
| 2008/0293996 A1* | 11/2008 | Evans et al. | 600/16 |
| 2009/0054723 A1* | 2/2009 | Khairkhahan et al. | 600/16 |
| 2009/0192539 A1* | 7/2009 | Lichtenstein | 606/191 |

* cited by examiner

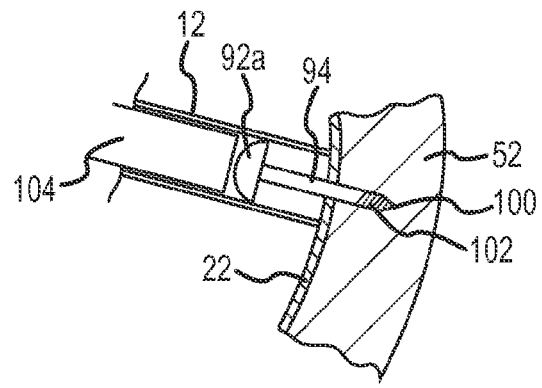
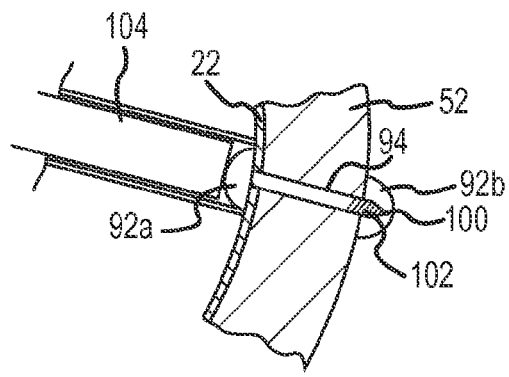
FIG.5A   FIG.5B
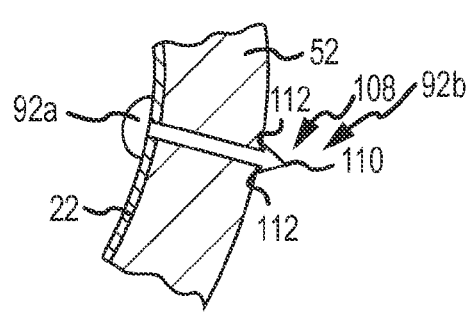
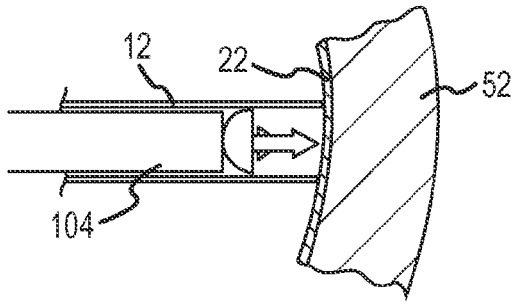
FIG.5C   FIG.5D
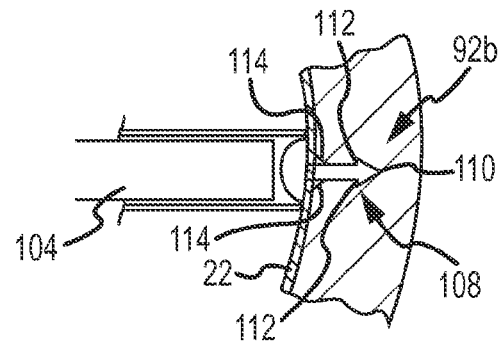
FIG.5E

APPARATUS AND METHODS FOR SUPPORTING CARDIAC ISCHEMIC TISSUE

BACKGROUND OF THE INVENTION

1. The Field of the Invention

This application relates to apparatus and methods for treating ischemic heart disease.

2. The Relevant Technology

Congestive heart failure is a condition that results in the inability of the heart to fill or pump blood effectively. Failure to treat congestive heart failure results in a gradual decline in heart function over time. Lifestyle changes such as an improved diet and increased physical activity can slow the progression of congestive heart failure. Certain drugs may also reduce the effects of the disease. However, the disease cannot presently be reversed. If untreated, congestive heart failure will ultimately require a complete heart transplant to prevent the death of the patient.

A specific manifestation of the disease is a weakening of the myocardium. As a result, the myocardium may become distended and sag. The weakened myocardium not only fails to contribute to the ability of the heart to pump blood, but also tends to expand during ventricular systole. The weakened region therefore causes a reduction of pressure within the ventricle and increases the volume of the ventricle at peak ventricular systole, thereby reducing the amount of blood flow.

BRIEF SUMMARY OF THE INVENTION

These and other limitations may be overcome by embodiments of the present invention, which relates generally to medical devices and methods for treating ischemic heart disease.

In one aspect of the present invention, an apparatus for supporting cardiac ischemic tissue includes a layer of biocompatible material defining a perimeter and a plurality of anchors adapted to secure to myocardial tissue positioned proximate the perimeter. A placement rod is detachably secured to the layer at an attachment point. A number of resilient reinforcing elements may be secured to the layer.

In another aspect of the invention, a layer of biocompatible material is positioned adjacent the ischemic tissue and anchored with respect to the ischemic tissue. This may include positioning a distal end of a placement rod secured to the layer adjacent the ischemic tissue, expanding the layer over the ischemic tissue, and detaching the placement rod from the layer.

In another aspect of the invention, an inflatable member is positioned adjacent the ischemic tissue and a filler material, such as memory foam, is injected adjacent the ischemic tissue. The filler material may be injected between a layer of biocompatible material anchored to the myocardium and the ischemic tissue.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 5A through 5E illustrate anchors for securing a scaffold to a myocardium in accordance with an embodiment of the present invention;

DETAILED DESCRIPTION OF THE PREFERRED EMBODIMENTS

Embodiments of the invention relate to apparatus, systems, and methods for supporting ischemic tissue. Embodiments of the invention may include supporting structure such as a patch or scaffold devices that can be deployed within the chamber of a heart. The supporting structure apposes a portion of the heart chamber and remove stress from the portion of the heart wall that is covered by or supported by the supporting structure. Providing supporting structure to weakened walls, for example myocardial tissue that is diseased by congestive heart failure, can mitigate the deleterious effects of the disease.

Figure 1A:
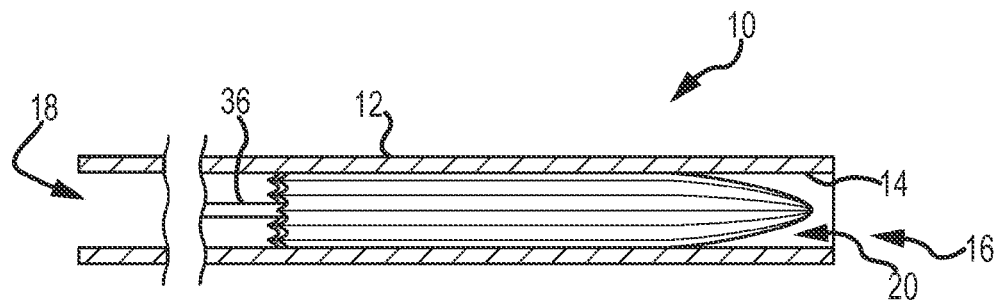
FIG. 1A is a side view of an assembly including a scaffold for supporting ischemic tissue positioned within a catheter in accordance with an embodiment of the present invention.
Figure 1B:
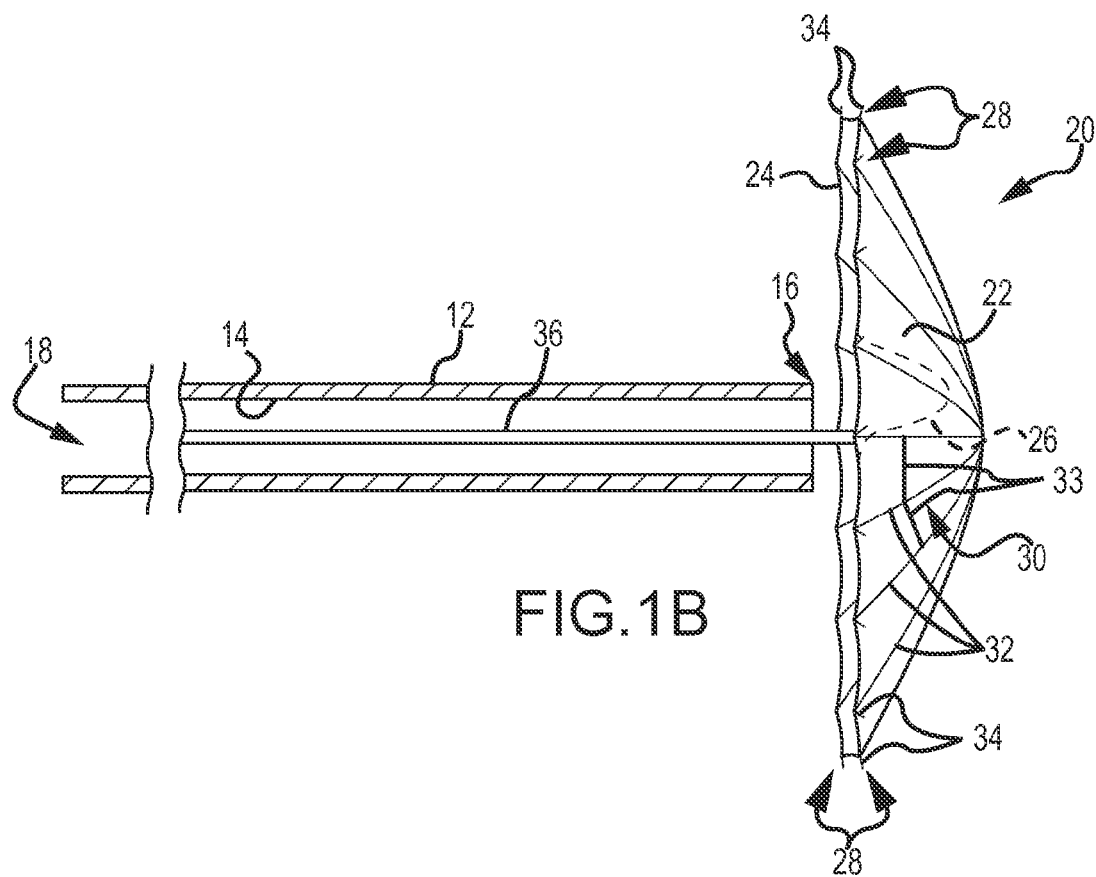
FIG. 1B is a side view of the assembly of claim 1A having the scaffold in a deployed configuration in accordance with an embodiment of the present invention.

Referring to FIGS. 1A and 1B, an assembly 10 may be used for the treatment of ischemic myocardial tissue of a heart by providing support for the ischemic tissue and mitigating reductions in the pumping capacity of the heart caused by the ischemic tissue or by disease to the ischemic tissue. The assembly 10 includes a delivery catheter 12 defining a lumen 14. The catheter is preferably sized to access the heart percutaneously. The catheter includes a distal end 16 positionable within the heart of a patient and a proximal end 18 located outside of a patient's body.

A scaffold 20 is positionable within the lumen 14 and has a compact (FIG. 1A) and deployed (FIG. 1B) configurations. The scaffold 20 includes a layer 22 of a biocompatible material. The layer 22 may be embodied as a continuous layer of material or may be embodied as a mesh or woven material.

The layer 22 may be either porous or nonporous. The layer 22 may include for example an open or closed cell foam material, or the like and may be formed of a polymer, metal, or other material having sufficient flexibility and toughness. The layer 22 may be formed of a biocompatible material or be coated with a biocompatible material. Examples of biocompatible materials may include polypropylene; poly(ester amide) (PEA); fluorinated polymers or copolymers such as polytetrafluoroethylene (PTFE), poly(vinylidene fluoride) and poly(vinylidene fluoride-co-hexafluoro propene); poly(hydroxyvalerate); poly(L-lactic acid) (PLLA); poly(ε-caprolactone); poly(lactide-co-glycolide) (PLGA); polyglycolide acid (PGA); poly(hydroxybutyrate); poly(hydroxyvalerate); poly(ethylene terephthalate); poly(hydroxybutyrate-co-valerate); polydioxanone; polyorthoester; poly(glycolic acid) (PGA); poly(D,L-lactic acid) (PLA); poly(glycolic acid-co-trimethylene carbonate); polyurethanes such as polyphosphoester urethane, poly(amino acids); poly(trimethylene carbonate); co-poly(ether-esters); polyphosphazenes; silicones; polyesters; polyolefins; polyisobutylene and ethylene-alphaolefin copolymers; vinyl halide polymers and copolymers such as polyvinyl chloride (PVC); polyvinyl ethers such as polyvinyl methyl ether; polyvinylidene chloride; polyacrylonitrile; poly(N-isopropylacrylamide); polyvinyl ketones; polyvinyl aromatics such as polystyrene, styrene sulfonate and acrylonitrile-styrene copolymers; polyvinyl esters such as polyvinyl acetate and polyvinylalcohol (PVA); polycarbonates; acrylonitrile butadiene (ABS) resins; ethylene-vinyl acetate copolymers; polyamides such as nylong (e.g., Nylon 66) and polycaprolactam; polyhydroxyethyl-methacrylate (pHEMA); poly(methyl methacrylate); poly(butyl acrylate); polyoxymethylenes; polyimides; polypropylene fumarate); polyethers; polyurethanes; polyurethane(ureas); poly-ε-caprolactone (PCL); biodegradable polyurethanes; biodegradable polyurethane(ureas); rayon; rayon-triacetate; and (Chitin), Chitosan, poly(glycolic acid-co-trimethylene carbonate), co-poly(ether-esters) (e.g. PEO/PLA), and biomolecules (such as fibrin, fibrinogen, elastin, silk, cellulose, starch, collagen (gelatine) and hyaluronic acid); stainless steel and cobalt-based alloys; precious and refractory metal elements and alloys; nitinol or other shape memory alloys, including layered or cored configurations to enhance mechanical or imaging properties, such as, but not limited to, platinum (Pt) covered by stainless steel or by elgiloy.

The layer 22 may be flat or may have a cupped shape such that it conforms to the lower portion of a ventricle or shape of other body lumen when the scaffold is deployed. The layer 22 may also have other more irregular shapes to conform to other portions of a ventricle. For example, a perimeter 24 may define a circle, ellipse, or other shape, having inlets 26 (shown by dotted line) positioned such that the layer 22 does not contact structures within the ventricle such as the papillary muscles and chordae tendonae. Alternatively, the layer 22 may be sufficiently flexible to bend around such structures or otherwise accommodate such structure without interfering with the function thereof.

Anchors 28 secured to the layer 22 may secure the layer to the tissue of the heart by attaching either to the ischemic tissue itself or to healthy tissue surrounding the ischemic tissue. In the illustrated embodiment, the anchors 28 are positioned at the perimeter 24 of the layer 22. However, anchors 28 may also be positioned within the perimeter 24 in an alternative embodiment or in addition to the anchors 28 positioned at the perimeter 24.

The layer 22 may be sufficiently stiff to maintain its shape in the absence of an external force. The layer 22 may also be sufficiently elastic to return to an undeformed shaped following elastic deformation. In some embodiments, the layer 22 may be coupled to a biasing frame 30 that urges the scaffold 20 into its deployed configuration once the scaffold 20 is removed from the lumen 14. The biasing frame 30 may urge the scaffold 20 into the deployed configuration due to an elastic biasing force caused by compression of the frame 30 during insertion within the lumen 14.

Alternatively, the biasing frame 30 may transition from the compact to the deployed configuration due to shape memory of the frame 30 in response to a change in temperature. For example, the frame 30 may include a shaped memory material ("SMM") or superelastic material. For example, the SMM can be shaped in a manner that allows for restriction to induce a substantially tubular, linear orientation while within the lumen 14, but can automatically retain the memory shape of the biasing frame once extended from the lumen 14. SMMs have a shape memory effect in which they can be made to remember a particular shape. Once a shape has been remembered, the SMM may be bent out of shape or deformed and then returned to its original shape by unloading from strain or heating. SMMs can be shape memory alloys ("SMA") or superelastic metals comprised of metal alloys, or shape memory plastics ("SMP") comprised of polymers.

An SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy. The nitinol and elgiloy alloys can be more expensive, but have superior mechanical characteristics in comparison with the copper-based SMAs. The temperatures at which the SMA changes its crystallographic structure are characteristic of the alloy, and can be tuned by varying the elemental ratios.

For example, the primary material of the biasing frame 30 can be of a NiTi alloy that forms superelastic nitinol. Nitinol materials can be trained to remember a certain shape, straightened in a shaft, catheter, or other tube, and then released from the catheter or tube to return to its trained shape. Also, additional materials can be added to the nitinol depending on the desired characteristic.

An SMP is a shape-memory plastic or polymer that can be fashioned into the biasing frame 30 in accordance with the present invention. When an SMP encounters a temperature above the glass transition temperature, the polymer makes a transition to a rubbery state. The elastic modulus can change more than two orders of magnitude across the glass transition temperature ("$T_g$"). Other transitions in a semi-crystalline copolymer such as a melt temperature ("$T_m$") can be used. Therefore the $T_g$ or $T_m$ of a shape memory copolymer can be used as a transition temperature ("$T_{tr}$"). As such, a SMP can be formed into a desired shape of the biasing frame 30 by heating it above the $T_{tr}$, fixing the SMP into the new shape, and cooling the material below $T_{tr}$. The SMP can then be arranged into a temporary shape by force and then resume the memory shape once the force has been applied. Examples of SMPs include, but are not limited to, biodegradable materials such as biodegradable polyurethanes, biodegradable polyurethane ureas, copolymers of poly(ε-caprolactone) and poly(butyl terephthalate), poly(ketone-co-alcohol), poly(ethylene-co-propene-co-carbonoxide), poly(ε-caprolactone) dimethyacrylate and n-butyl acrylate, star-shaped oligoesters, and non-biodegradable polymers such as polynorborene, polyisoprene, polystyrene block copolymers, poly(1,4-butadiene), PET-PEO block copolymer, non-biodegradable polyurethane-based materials, vinyl acetate-polyester-based compounds, and others yet to be determined. As such, any SMP can be used in accordance with the present invention.

Also, it can be beneficial to include at least one layer of an SMA and at least one layer of an SMP to form a multilayered body; however, any appropriate combination of materials can be used to form a multilayered medical device.

The biasing frame 30 can be comprised of a variety of known suitable deformable materials, including stainless steel, silver, platinum, tantalum, palladium, cobalt-chromium alloys such as L605, MP35N, or MP20N, niobium, iridium, molybenum, rhenium, any equivalents thereof, alloys thereof, and combinations thereof. The alloy L605 is understood to be a trade name for an alloy that includes about 53% cobalt, 20% chromium, 15% tungsten and 10% nickel. The alloys MP35N and MP20N are understood to be trade names for alloys of cobalt, nickel, chromium and molybdenum. More particularly, MP35N generally includes about 35% cobalt, 35% nickel, 20% chromium, and 10% molybdenum, and MP20N generally includes about 50% cobalt, 20% nickel, 20% chromium and 10% molybdenum.

Also, the biasing frame 30 can include a suitable biocompatible polymer in addition to or in place of a suitable metal. The polymeric biasing frame 30 can include a biocompatible material, such as biostable, biodegradable, or bioabsorbable materials, which can be either plastically deformable or capable of being set in the deployed configuration. If plastically deformable, the material can be selected to allow the medical device (e.g., stent) to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the required catalyst to set or cure the polymer. Biocompatible polymers are well known in the art, and examples are recited with respect to the polymeric matrix. Thus, biasing frame 30 can be prepared from a biocompatible polymer.

Moreover, the biasing frame 30 can include a radiopaque material to increase visibility during placement. Optionally, the radiopaque material can be a layer or coating any portion of the biasing frame 30. The radiopaque materials can be platinum, tungsten, silver, stainless steel, gold, tantalum, bismuth, barium sulfate, or a similar material.

In the illustrated embodiment, the biasing frame 30 includes wires 32, such as nitinol wires 32, arranged at different angles and crossing one another to form an "umbrella frame." The wires 32 may have undeformed, or memory, shape that is straight. Alternatively, the wires 32 may have an undeformed, or memory, shape that is bent to the same or a larger radius of curvature as a cupped layer 22 or a portion of the ventricle in which the scaffold 22 is placed. As noted above the wires 32 may include a polymer material, such as SMP materials such that the memory shape of the wires 32 corresponds to the deployed configuration and the deformed shape corresponds to the compact configuration. The biasing frame 30, such as the wires 32 of the biasing frame 30, or a mesh comprising the layer 22 are configured into a final shape utilizing a suitable forming device and shape setting techniques well known in the art. Alternatively the material condition of the layer 22 may be designed such that the layer 22 itself is shape memory and does not depend on SMA properties of a frame 30 to retain its properties after deformation. For example the wires may be held in place by mechanical means, including by tack welding, at key points to influence the final shape of the layer 22. The wires 32 of the frame 30 may further include ribs 33 extending therebetween at a middle portion thereof. The ribs 33 may be parallel or cross one another.

In some embodiments, the anchors 28 may be embodied as hooked portions 34 formed on the ends of the wires 32 and positioned adjacent the perimeter 24 of the layer 22 such that they engage either the ischemic tissue, or healthy tissue adjacent the ischemic tissue, of a placement site within the ventricle, or other portion of the heart. The hooked portions 34 may be embodied as sharp, e.g. between 80 and 110 degree, bends within the wires 32 and may further include barbs or other structures to facilitate retention within the myocardium.

Figure 2:
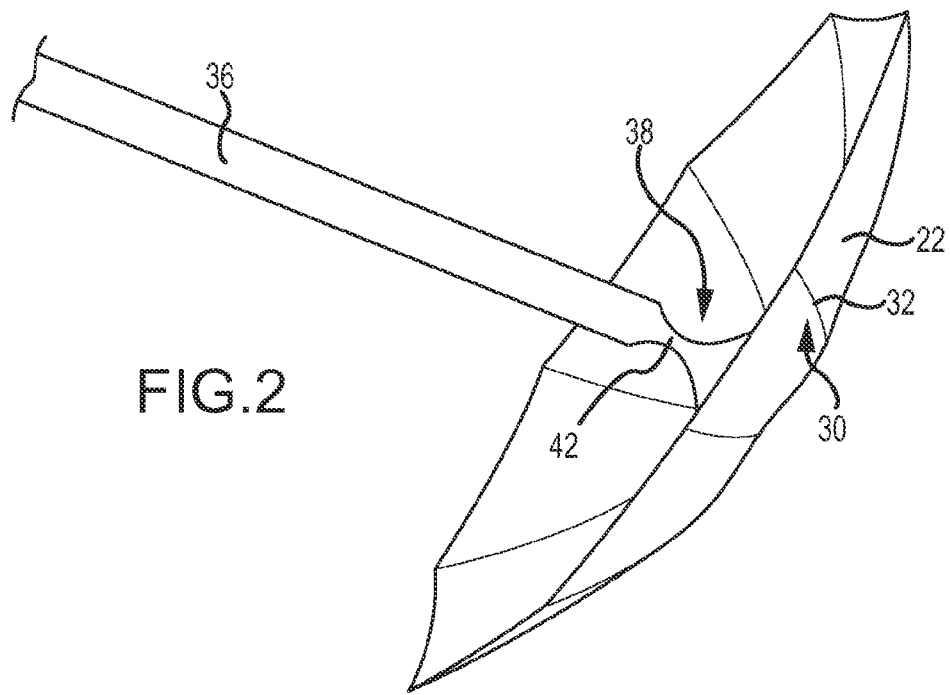
FIG. 2 is an isometric view of the scaffold of FIGS. 1A and 1B in accordance with an embodiment of the present invention.

Referring to FIG. 2, while still referring to FIGS. 1A and 1B, the layer 22 and/or biasing frame 30 may be detachably secured to a placement rod 36. The placement rod 36 may extend from the scaffold 20 to the proximal end 18 of the catheter to enable a physician to move the scaffold 20 externally from the patient's body. A distal end 38 of the placement rod 36 secures to the scaffold 20. The placement rod 36 may be detachably secured to the layer 22 and/or biasing frame 30 by means of any number of detachable attachment means. For example, in the illustrated embodiment, a narrowed and readily broken portion 42 of the rod 36 itself serves as the detachment mechanism. In such embodiments, the distal end 38 of the rod 36 may be secured to the layer 22 and/or biasing frame 30 by means of an adhesive or welding such that it is not readily removable.

Figure 3:
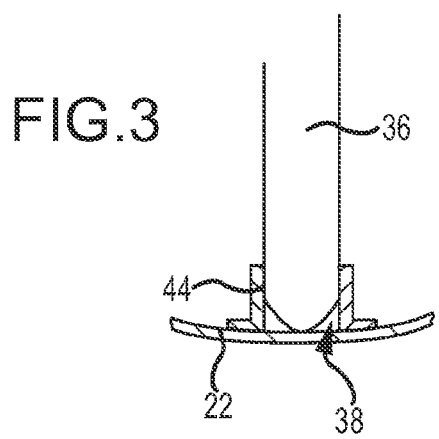
FIG. 3 is side view of a fastening system for detachably securing a placement rod to a scaffold in accordance with an embodiment of the present invention.

Referring to FIG. 3, alternatively, the rod 36 may secure to the layer 22 and/or biasing frame 30 by means of threads. For example, the layer 22 and/or biasing frame 30 may have a threaded socket 44 for receiving the distal end 38 of the rod 36. In yet another alternative embodiment, the rod 36 is secured to the layer 22 and/or biasing frame 30 by means of a press fit, such as an unthreaded socket 44 secured to the layer 22 and/or biasing frame 30. In such embodiments one or both of the rod 36 and unthreaded socket 44 may have a smaller inner diameter than the outer diameter of the road 36 and include an elastic material such that a biasing force retains the rod 36 within the socket 44.

Figure 4A:
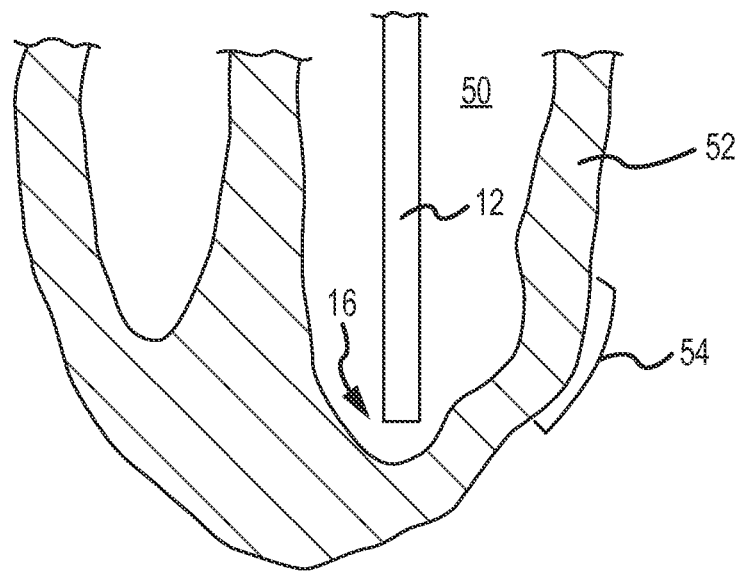
FIGS. 4A through 4I illustrate a method for placement of a scaffold adjacent ischemic tissue in accordance with an embodiment of the present invention.

A scaffold 20 may be deployed according to the method illustrated in FIGS. 4A through 4J. Referring specifically to FIG. 4A, the distal end 16 of the catheter 12 may be positioned within the ventricle 50 adjacent a portion of the myocardium 52 including an ischemic area 54. The scaffold 20 may be positioned within the distal portion of the catheter 12 at the time of insertion of the catheter 12 or may be guided through the lumen 14 to the distal end 16 following positioning of the catheter 12 within the heart 50 as shown in FIG. 4A.

Figure 4B:
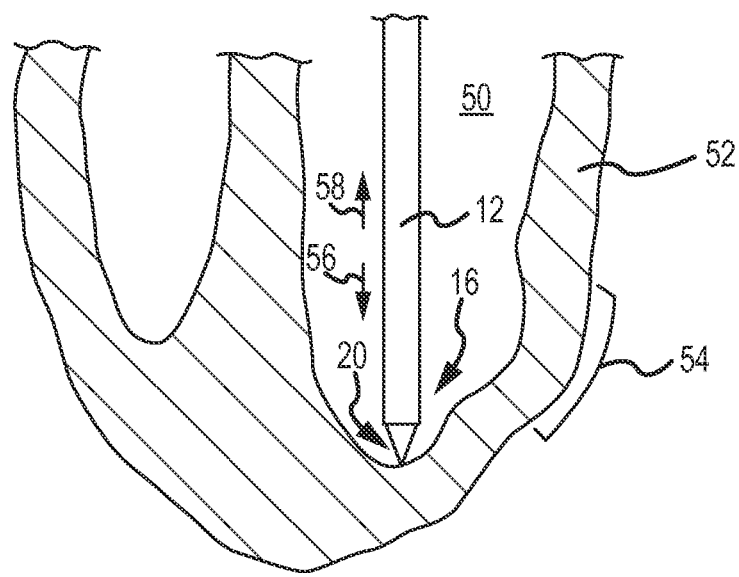

Referring to FIG. 4B, the scaffold 20 may be urged in a distal direction 56 while the catheter is drawn in the proximal direction such that the scaffold 20 exits the lumen 14 of the catheter 12. This may be accomplished by applying a force on the catheter in the proximal direction 58 while applying a force to the placement rod 36 in the distal direction 56.

Figure 4C:
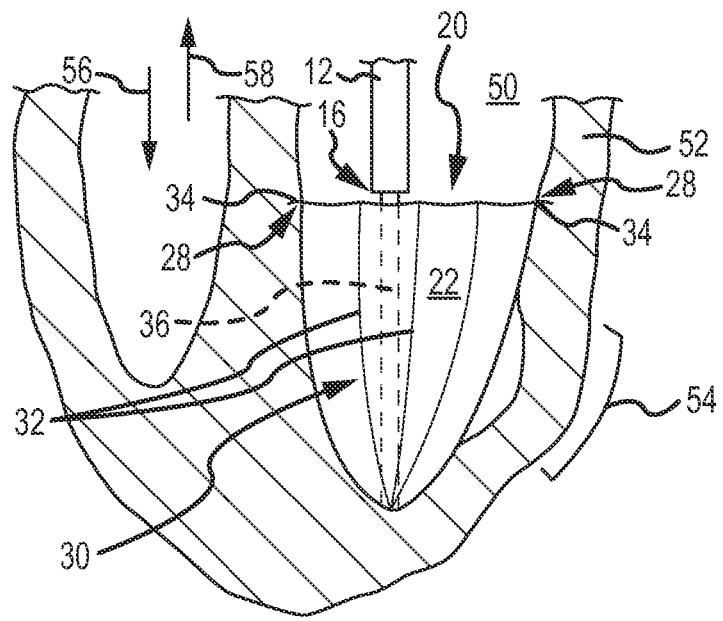

Referring to FIG. 4C, upon exiting the lumen 14, the scaffold 20 may expand from the compact configuration to the deployed configuration insofar as permitted by the ventricle 50. As noted above, expansion of the scaffold 20 to the deployed configuration may be due to elastic expansion of the layer 22 or biasing frame 30 or due to reversion of the biasing frame 30 to a memory shape due to a temperature change. Upon expansion of the scaffold 20 to the deployment configuration, the anchors 28 may be urged into the myocardium 52 of the ventricle 50. As noted above, the anchors 28 may be embodied as hooked portions 34 of wires 32. The hooked portions 34 may therefore be urged into the myocardium 52 responsive to elastic or shape-memory expansion of the wires 32. Placement of the scaffold 20 as shown in FIG. 4C may include positioning any inlets 26 (See FIG. 1B) around structures within the ventricle 50, such as the chordae tendonae or papillary muscles.

Figure 4D:
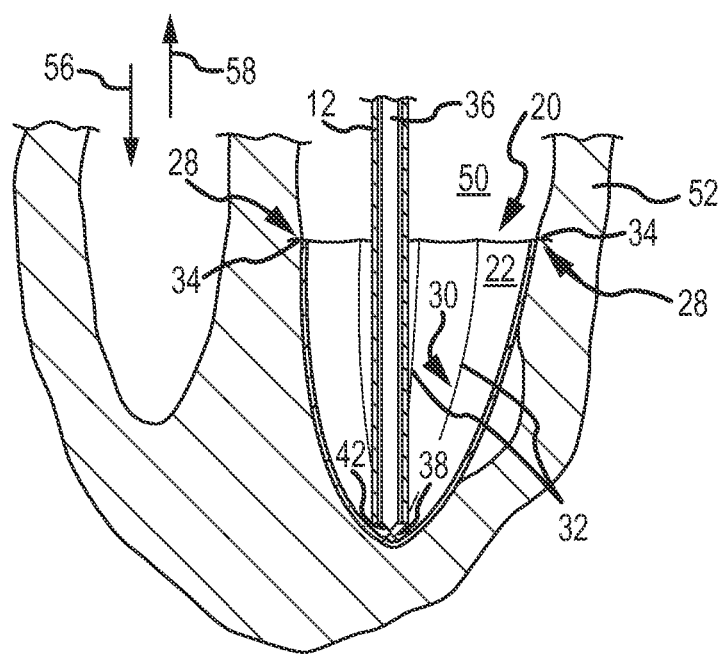

Referring to FIG. 4D, the placement rod 36 may then be detached from the scaffold 20. In the illustrated embodiment, this is accomplished by urging the catheter 12 in the distal direction 56 into engagement with the layer 22 and/or biasing frame 30 to retain the scaffold 20 in position and drawing the placement rod 36 in the proximal direction 58 with sufficient force to break the narrowed portion 42 or to urge the distal end 38 of the placement rod 36 out of the socket 44. In embodiments where threaded engagement is used, removal of the placement rod 36 may include rotation therefore to unthread the distal end 38 from the threaded socket 44.

Figure 4E:
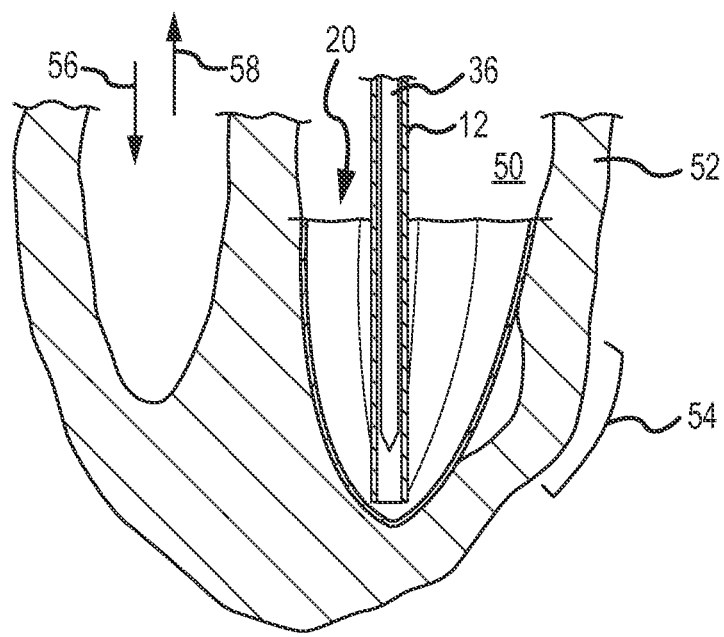

Referring to FIG. 4E, following detachment, the catheter 12 and placement rod 36 may be withdrawn, leaving the scaffold 20 in place.

Figure 4F:
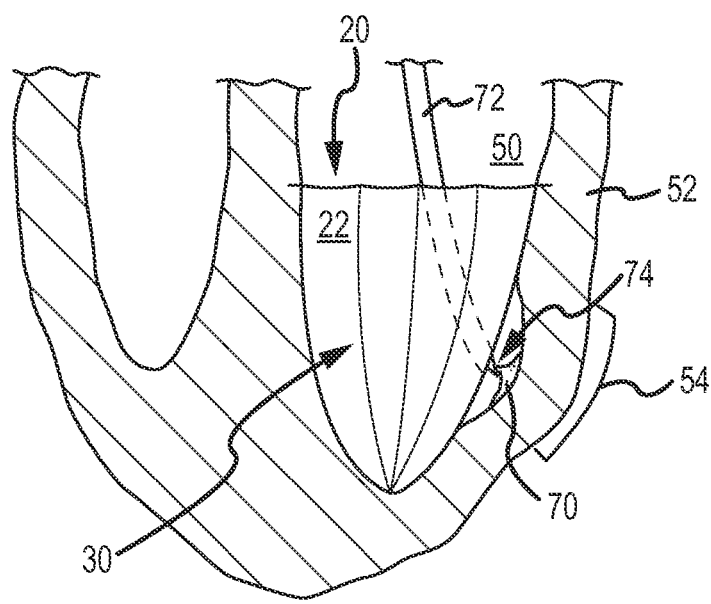
Figure 4G:
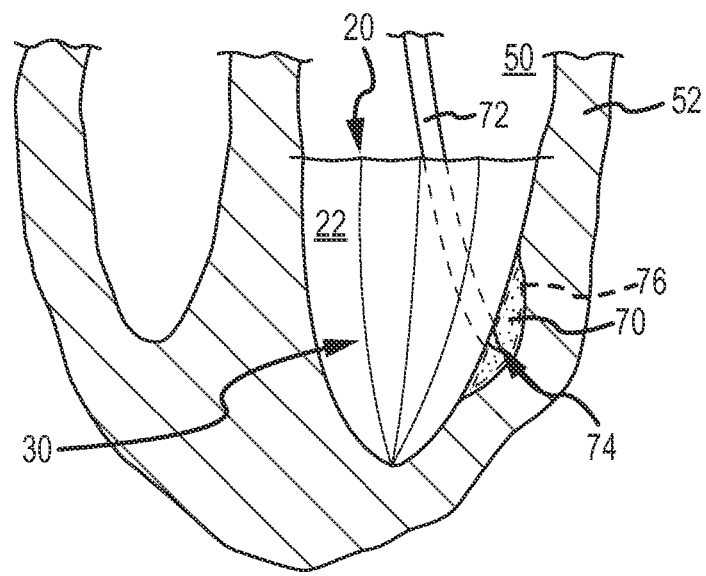

Referring to FIG. 4F, in some embodiments, the ischemic area 54 may be further supported by injecting a filler material 70, such as memory foam within a space between the scaffold 20 and the ischemic area 54. The memory foam may be formed of a visco-elastic polymer such as polyurethane foam or other suitable biocompatible polymer. In such embodiments, a delivery tube 72 may be inserted into the ventricle. A distal end 74 of the delivery tube 72 may be sharpened to facilitate penetration of the layer 22. Alternatively, the layer 22 may define an aperture prior to placement for receiving the distal end 74 of the delivery tube 72 such that a sharpened distal end 74 is not needed. The distal end 74 of the delivery tube 72 penetrates the layer 22 and filler material 70 is injected through the tube 72 into the space between the layer 22 and the ischemic area 54. The distal end 74 of the delivery tube 72 may include a radiopaque material to facilitate placement adjacent the ischemic area 54. As shown in FIG. 4G, an amount of filler material 70 may be injected sufficient to occupy the increased volume 76 created by distention or sagging of the ischemic area 54.

Figure 4H:
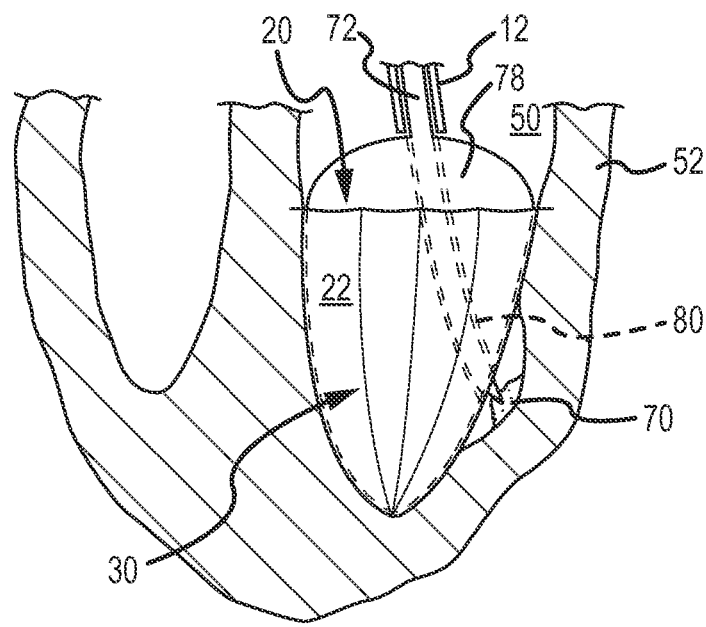

Referring to FIG. 4H, in some embodiments, an inflatable member 78 is delivered through the catheter 12 and positioned adjacent the scaffold prior to injection of the filler material 70. In some embodiments, the inflatable member 78 may be inflated to occupy a substantial portion of the volume defined by the ventricle 50 and reduce deformation of the scaffold 20 due to pressure from the filler material 70 during injection. In some embodiments, the inflatable member 78 remains inflated as shown in FIG. 4H until the filler material 70 has cured. The inflatable member 78 may define a channel 80 permitting passage of the delivery tube therethrough to the ischemic area 54. After the filler material 70 has cured the inflatable member 78 may be deflated and withdrawn through the catheter 12.

Figure 4I:
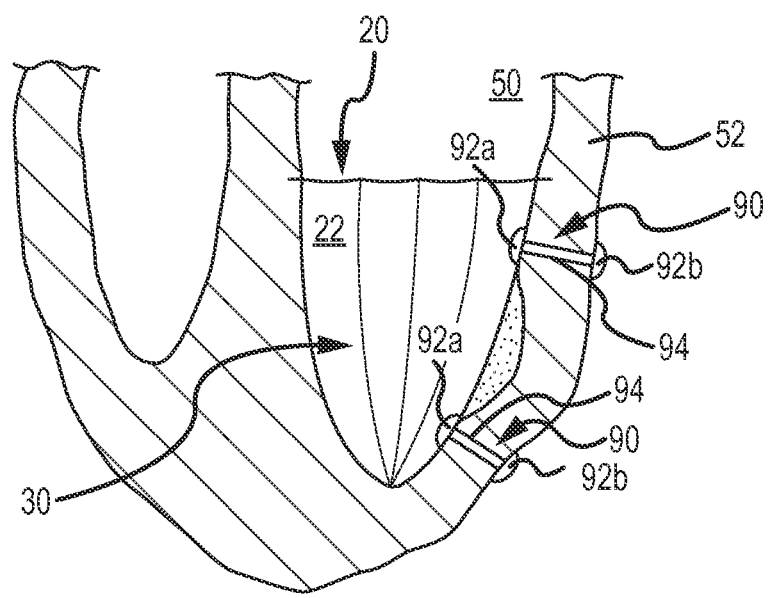

Referring to FIG. 4I, in some embodiments, one or more additional anchors 90 may be placed to retain the scaffold 20 adjacent the ischemic area. In the illustrated embodiment, the anchors 90 capture the scaffold and myocardium 52 between heads 92a and 92b, with the heads 92a positioned within the ventricle abutting the layer 22 and the heads 92b positioned outside the ventricle abutting the myocardium 52. In the illustrated embodiment, the anchors 90 are positioned within healthy tissue adjacent the ischemic area 54. A coupling portion 94 may penetrate the myocardium 52 and secure to the heads 92a, 92b to prevent separation thereof.

The head 92a and/or coupling portion 94 may be formed of, or be coated with, a material promoting sealing between the layer 22 and the head 92a and/or coupling portion 94. For example, a flexible, elastic polymer providing a biasing force against the layer 22 may be used. Alternatively, a gel or other semiliquid substance may be used to coat the coupling portion 94 and/or head 92a, 92b in order to promote sealing between the coupling portion 94 and the layer 22.

Referring to FIGS. 5A through 5D, various fasteners may be used as the anchors 90. Referring specifically to FIG. 5A, in some embodiments, the head 92b is secured to the coupling portion 94 by means of threads, press fit, pressure sensitive adhesive, or the like. In such embodiments, the head 92a having the coupling portion 94 secured thereto may be delivered within the ventricle through a catheter 12. The coupling portion 94 may have a sharpened end 100 and threads 102 for threaded engagement with the head 92b. The head 92a having the coupling portion 94 secured thereto may be positioned within a catheter 12. The coupling portion may then be urged through the layer 22 and myocardium 52 such that the end 100 protrudes from the myocardium 52. A push rod 104 may be inserted through the catheter 12 in order to urge the coupling portion 94 through the layer 22 and myocardium 52. As shown in FIG. 5B, the head 92b may then be secured to the coupling portion 94. For example, the head 92b may define a threaded aperture 106 for receiving the threads 102 of the coupling portion 94. Alternatively, the head 92b may secure to the coupling portion 94 by means of a press fit, snap-on connection, or the like.

Referring to FIG. 5C, in an alternative embodiment, the head 92b may be replaced with a barbed end 108 including a pointed distal end 110 and laterally extending barbs 112. In some embodiments, the barbed end 108 may be embodied as a conical portion secured to the distal end of the coupling portion 94, where the conical portion has a diameter at its widest point that is greater than that of the coupling portion 94. The anchor 90 of FIG. 5C may be positioned by urging the anchor 90 through a catheter 12 as shown in FIG. 5D using a push rod 104 to urge the barbed end 108 through the layer 22 into the myocardium 52 such that the barbed end 108 protrudes from the myocardium 52.

Referring to FIG. 5E, in some embodiments, the coupling portion 94 may have a length such that the barbed end 108 does not protrude from the myocardium 52, bur rather remains embedded within the myocardium 52. In some embodiments, barbs 114 may be positioned adjacent the head 92a such that the layer 22 is captured between the barbs 114 and the head 92a.

Figure 6A:
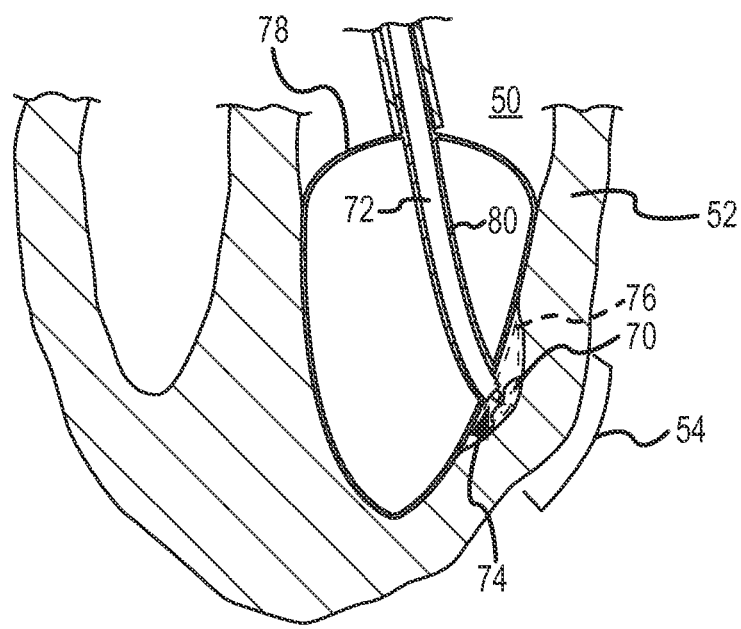
FIGS. 6A through 6C illustrate a method for forming a scaffold within a heart using a polymer in accordance with an embodiment of the present invention.
Figure 6B:
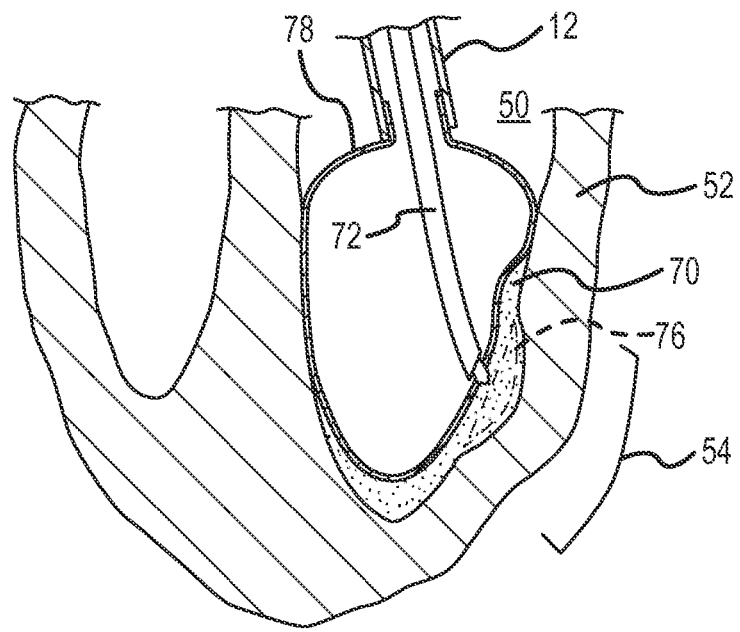
Figure 6C:
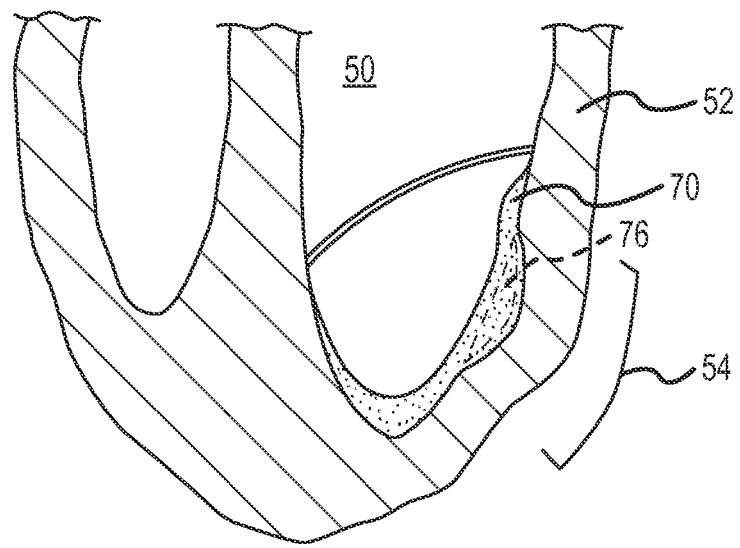

Referring to FIGS. 6A through 6C, in some embodiments, a filler 70, such as memory foam, may be delivered to adjacent the ischemic area 54 without first positioning a scaffold 20 within the ventricle. Referring specifically to FIG. 6A, an inflatable member 78 may be positioned within the ventricle 50 and inflated. A delivery tube 72 may be inserted to the ischemic area 54, such as by passing the delivery tube 72 through a channel 80 passing through the inflatable member 78. Filler material may then be delivered through the distal end 74 to substantially occupy the distended volume 76 of the ischemic area 54. In some embodiments, the filler material 70 may also flow around the inflatable member 78 to form a cupped shape covering a lower portion of the ventricle 50, as shown in FIG. 6B. After the filler material 70 is cured, the inflatable member 78 may be deflated. The inflatable member 78 and delivery tube 72 may be withdrawn leaving the filler material 70 in the configuration shown in FIG. 6C. In some embodiments, anchors 90, such as illustrated in FIGS. 5A through 5E, may be used to anchor the filler material to the myocardium 52 after the filler material 70 is cured.

Figure 7:
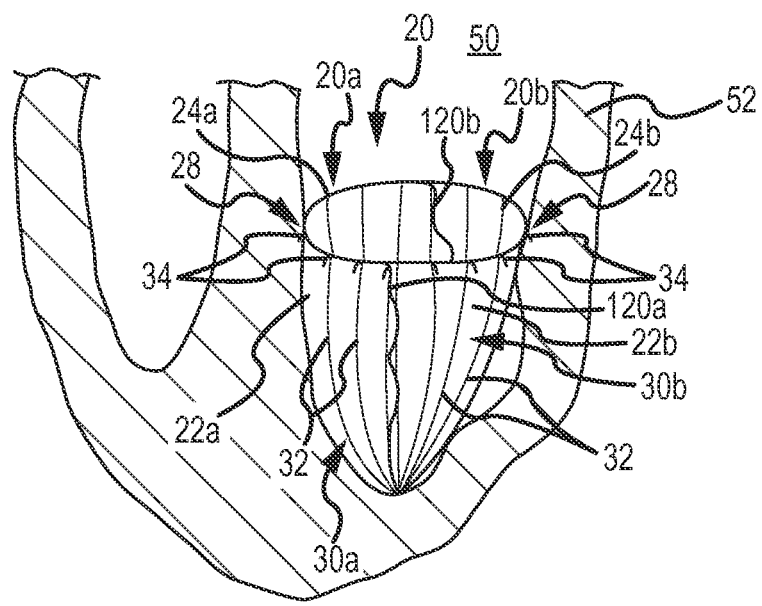
FIG. 7 is an isometric view of a scaffold including two independently placed portions in accordance with an embodiment of the present invention.

Referring to FIG. 7 in some embodiments the scaffold 20 may be formed of two or more scaffold portions 20a, 20b inserted separately into the ventricle 50. In such embodiments, the layer 22 may include layer portions 22a, 22b of biomaterial each forming part of one of the scaffold portions 20a, 20b, respectively, and sized to cover a portion of the myocardium 52. The layer portions 22a, 22b may further include edges 120a, 120b that interface with one another to mesh the layer portions 22a, 22b with one another. As with the embodiment including a single scaffold 20, the scaffold portions 20a, 20b may include inlets 26 that are positioned around structures within the ventricle 50, such as the chordae tendonae or papillary muscles, when the scaffold portions 20a, 20b are positioned within the heart.

Figure 8:
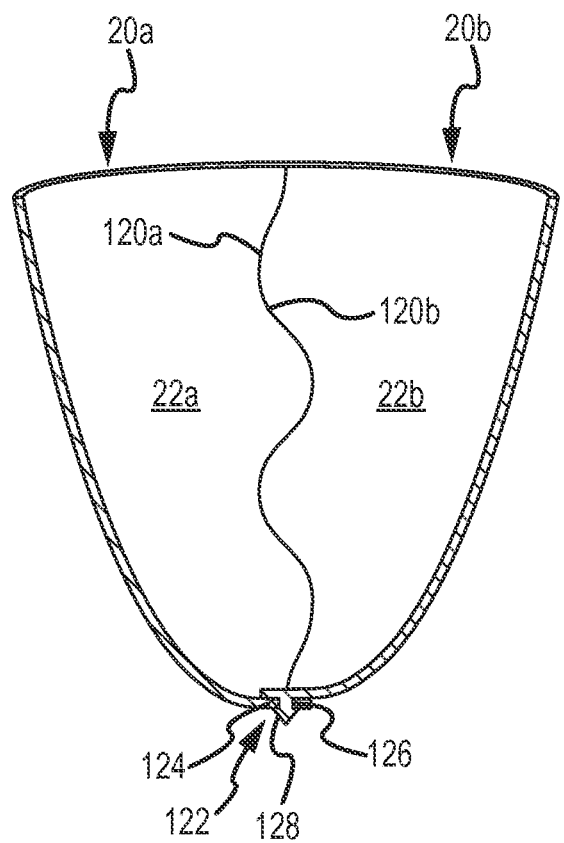
FIG. 8 is a side cross-sectional view of the scaffold of FIG. 7 including a fastener for securing the portions to one another.

The embodiment of FIG. 8 may include a biasing frame 30 including frame portions 30a, 30b forming part of the scaffold portions 20a, 20b, respectively. The frame portions 30a, 30b may comprise nitinol wires 32 arranged to define a shape corresponding to a portion of a ventricle 50. In the illustrated embodiment, the nitinol wires 32 radiate from a common hub to form a portion of a cupped shape.

The layers 22a, 22b may also include anchors 28 secured along the perimeters 24a, 24b thereof, or located within the perimeters 24a, 24b. The anchors 28 be embodied as hooked portions 34 formed on nitinol wires 32 of the biasing frame 30.

Referring to FIG. 8, in some embodiments, one or more fasteners 122 may secure the scaffold portions 20a, 20b to one another. For example, the scaffold portion 20a may include an aperture 124 sized to receive a post 126 having a lip 128 having a diameter larger than that of the aperture such that elastic deformation is required to insert the post 126 and lip 128 through the aperture 124.

Figure 9A:
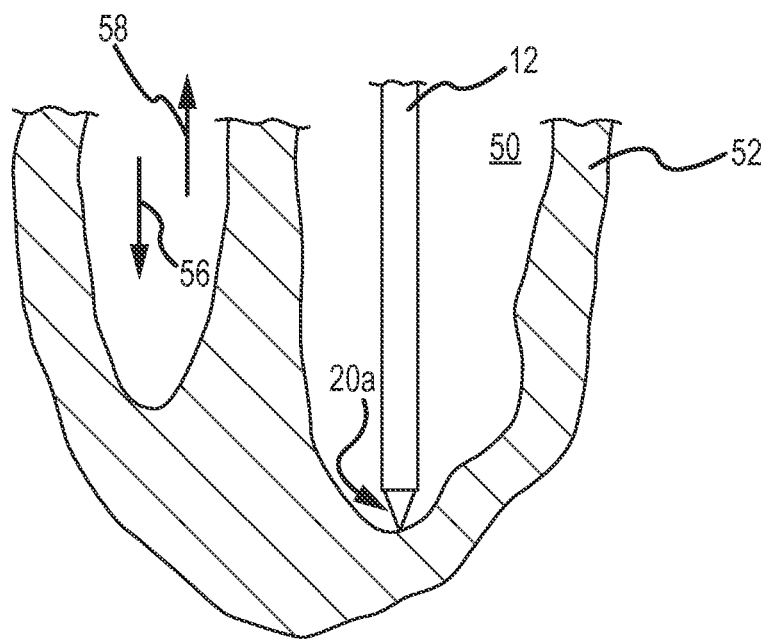
FIGS. 9A through 9K illustrate a method for positioning the scaffold of FIG. 7 adjacent ischemic tissue in accordance with an embodiment of the present invention.

A scaffold 20a including separate scaffold portions 20a, 20b may be placed within a ventricle according to a method illustrated in FIGS. 9A through 9K. Referring specifically to FIG. 9A, a catheter 12 may be inserted within the ventricle 50. A scaffold portion 20a may also be inserted into the ventricle through the catheter 12. The scaffold portion 20a may be positioned within the distal portion of the catheter 12 at the time of insertion or may be urged to the distal portion of the catheter 12 following insertion of the catheter 12 to the position shown in FIG. 9A.

Figure 9B:
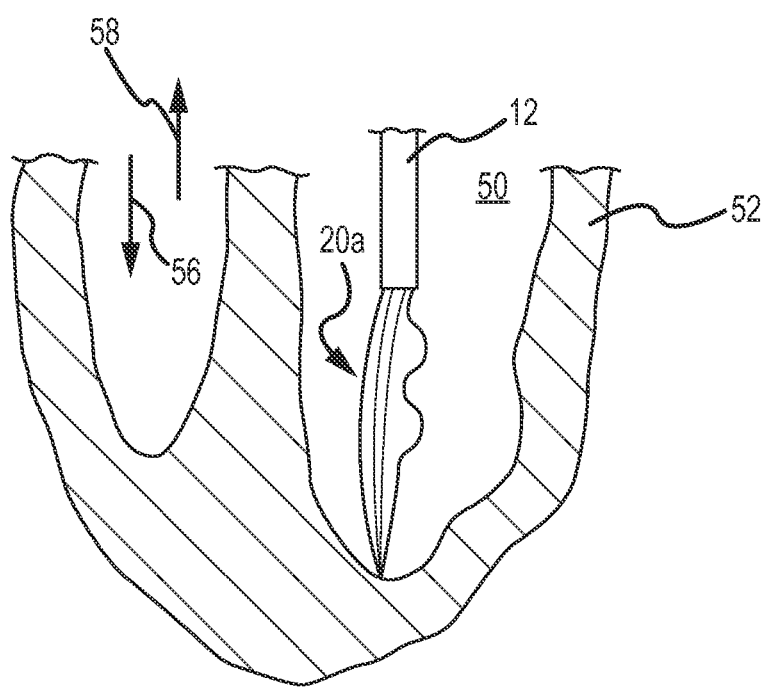
Figure 9C:
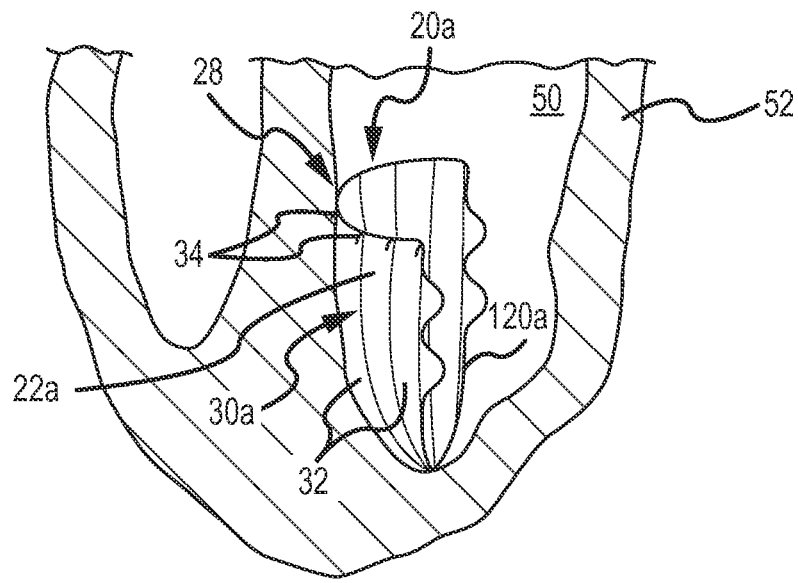

Referring to FIG. 9B, the scaffold portion 20a may be urged outwardly from the catheter 12. The catheter 12 may be withdrawn simultaneously with urging of the scaffold portion 20a from the catheter 12. Referring to FIG. 9C, as the scaffold portion 20a is urged outwardly from the catheter 12 the scaffold portion 20a may expand to a deployed configuration from a compact configuration sized to fit within the lumen 14 of the catheter 12. Expansion of the scaffold portion 20a may be due to elastic expansion of the layer portion 22a or frame portion 30a or due to shape-memory of the frame portion 30a caused by a change in temperature.

As the scaffold 20a expands form the compact configuration to the deployed configuration, anchors 28 may be urged into the myocardium 52. This may include urging of hooked portions 34 of the nitinol wires 34 into the myocardium 52 due to elastic or shape-memory expansion of the wires 34.

Figure 9D:
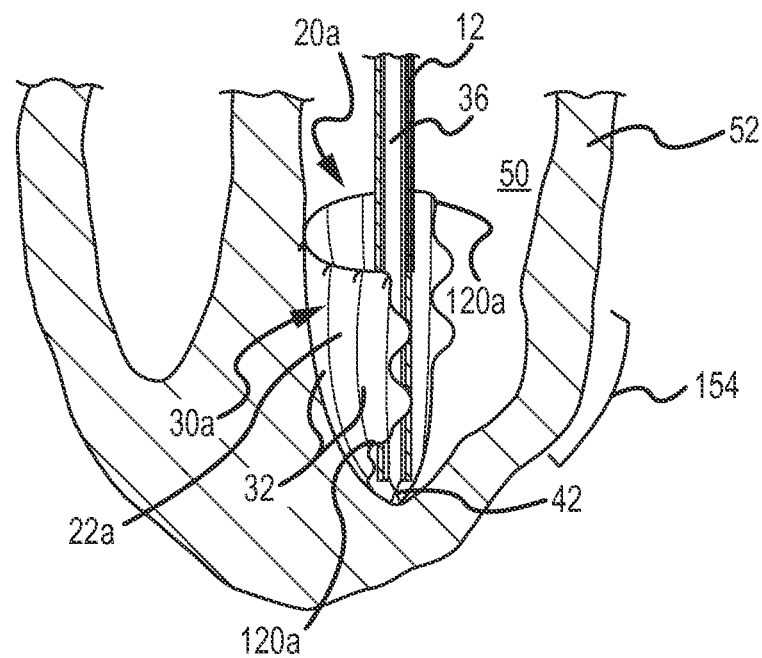

Referring to FIG. 9D, the scaffold portions 20a and 20b may be positioned using placement rods 36 extending from the proximal end of the catheter 12 to the scaffold portion 20a. The placement rods 36 may be secured to the scaffolds 20a, 20b by means of a narrowed and readily broken portion 42 of the rod 36 itself that serves as a detachment mechanism. In such embodiments, the distal end 38 of the rod 36 may be secured to the layer portion 22a, 22b and/or biasing frame portion 30a, 30b by means of an adhesive or welding such that it is not readily removable.

Alternatively, the rod 36 may secure to the layer portion 22a, 22b and/or biasing frame 30a, 30b by means of threads. For example, the layer portion 22a, 22b and/or biasing frame 30a, 30b may have a threaded socket 44 for receiving the distal end 38 of the rod 36, as shown in FIG. 3. In yet another alternative embodiment, the rod 36 is secured to the layer portion 22a, 22b and/or biasing frame 30a, 30b by means of a press fit, such as an unthreaded socket 44 secured to the layer portion 22a, 22b and/or biasing frame 30a, 30b. In such embodiment, one or both of the rod 36 and unthreaded socket 44 may have a smaller inner diameter than the outer diameter of the road 36 and include an elastic material such that a biasing force retains the rod 36 within the socket 44.

Figure 9E:
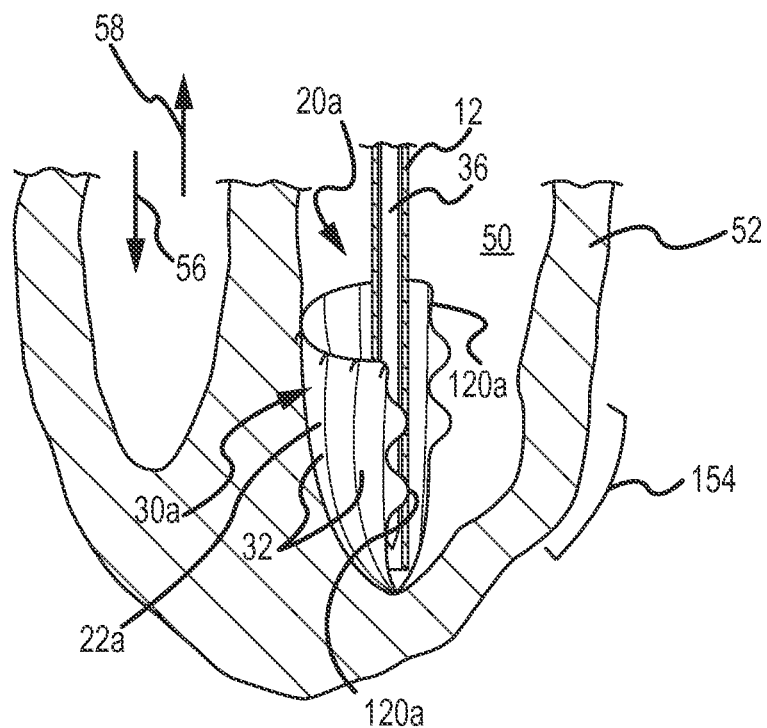

As shown in FIG. 9E, the placement rod 36 may be detached from the scaffold portion 20a by urging the placement rod 36 in the proximal direction 58 while urging the catheter 12 in the proximal direction into engagement with the layer 22 or biasing frame 30 such that the narrowed portion 42 breaks for the distal end 38 is urged out of a socket 44. Alternatively, where the placement rod 36 includes a threaded distal end 38, removal of the placement rod 36 may include rotating the placement rod 36 relative to the socket 44.

Figure 9F:
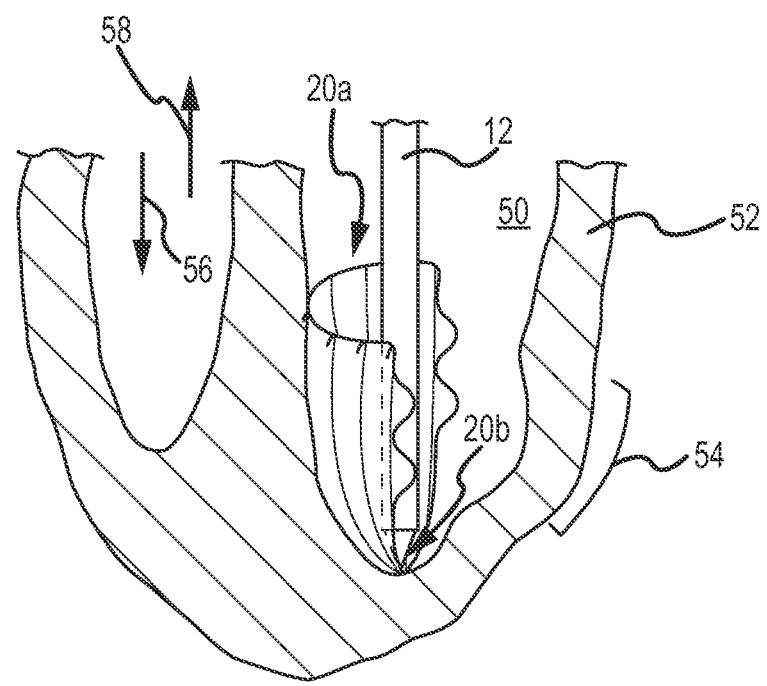

Referring to FIG. 9F, following placement of the scaffold portion 20a, one or more other scaffold portions 20b may be placed within the ventricle 50. A catheter 12 having the scaffold portion 20b positioned therein may be inserted into the ventricle 50. Insertion of the catheter and scaffold portion 20b may include coupling the scaffold portion 20b to the scaffold portion 20a by means of the fastener 122 by inserting the post 126 having a lip 128 and secured to one of the scaffold portions 20a, 20b into the aperture 124 defined by the other of the scaffold portions 20a, 20b.

Figure 9G:
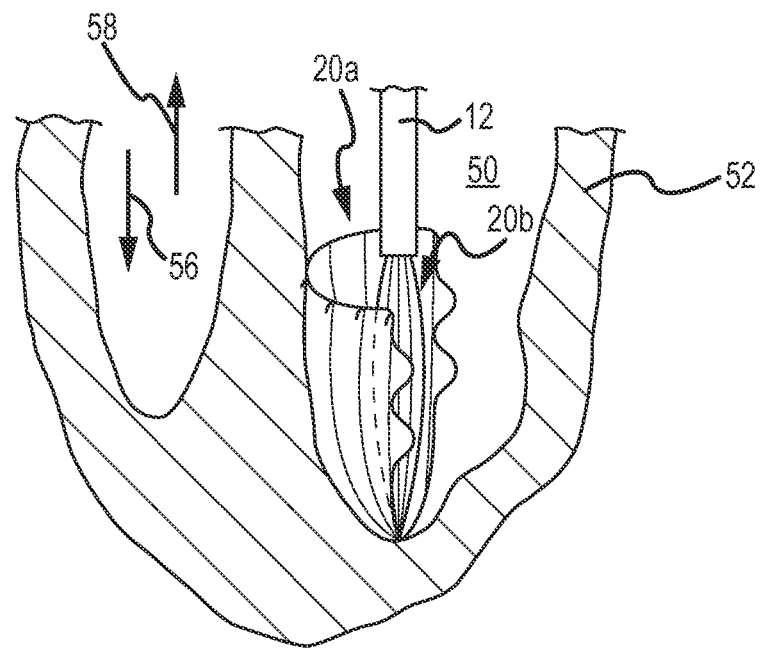

Referring to FIG. 9G, the scaffold portion 20b may be urged outwardly from the catheter 12 by applying force in the distal direction 56 to a placement rod 36 secured to the scaffold portion 20b while withdrawing the catheter 12 in proximal direction 58. The placement rod 36 may be detached from the scaffold portion 20a in the same manner as for the scaffold portion 20a shown in FIGS. 9D and 9E.

Referring to again to FIG. 7, upon exiting the catheter 12 the scaffold portion 20b may expand from a compact configuration to a deployed configuration covering a portion of the myocardium 52 of the ventricle 50. As with the scaffold portion 20a, expansion of the scaffold portion 20b may be due to elastic expansion of the layer 22 or biasing frame 30 or due to shape-memory expansion of the biasing frame 30 due to a change in temperature.

Figure 9H:
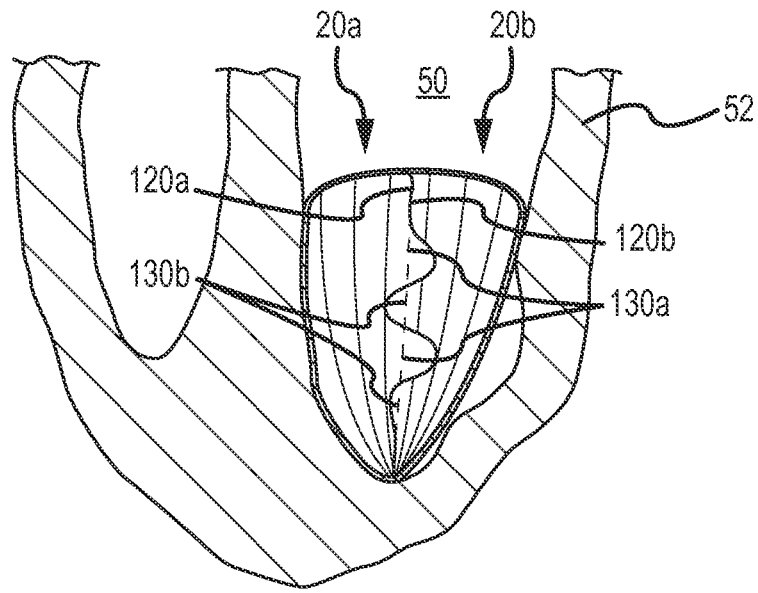
Figure 9I:
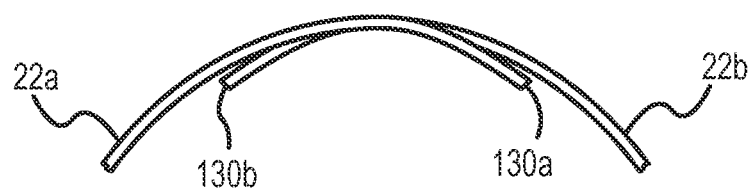
Figure 9J:
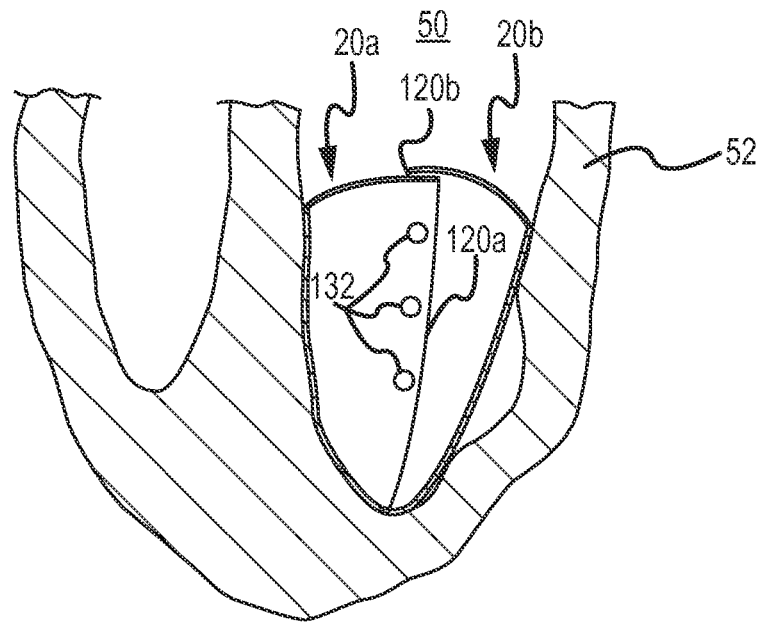
Figure 9K:
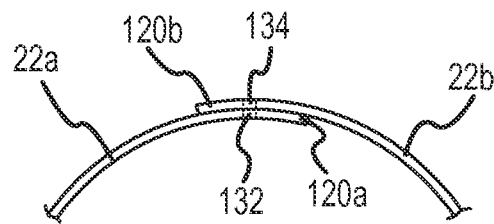

Referring to FIGS. 9H and 9I, the edges 120a, 120b of the scaffold portions 20a, 20b may mesh with one another. For example, the edges 120a may bear tabs 130a that interlock with tabs 130b of the edge 120b. Referring to FIGS. 9J and 9K, in an alternative embodiment, magnets or magnetic material 132 is secured to the scaffold portion 20a near the edges 120a and magnetically adheres to magnetic material 134, or magnets 134, secured near the edges 120b of the layer of the scaffold 20b.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for supporting ischemic tissue, the method comprising:
   positioning a first layer of biocompatible shape memory material sized to cover a portion of the myocardium within a heart;
   positioning a second layer of biocompatible material adjacent the first layer, the second layer having at least one edge that interlocks with at least one edge of the first layer to form one substantially continuous layer, where the at least one edge of the first layer that interlocks with the second layer, and the at least one edge of the second layer that interlocks with the first layer both extend from an apex of the substantially continuous layer to a proximal end of the substantially continuous layer;
   expanding at least one of the first and second layers over the ischemic tissue; and
   anchoring the layers with respect to the ischemic tissue.

2. The method of claim 1, wherein positioning the first or second layers of biocompatible material comprises:
   positioning a distal end of a placement rod adjacent the ischemic tissue, the distal end of the placement rod being secured to the first or second layer; and
   detaching the placement rod from the first or second layer.

3. The method of claim 2, wherein expanding at least one of the first and second layers over the ischemic tissue comprises urging the placement rod and the first or second layer outwardly from a catheter such that the first or second layer is enabled to expand.

4. The method of claim 2, wherein detaching the placement rod from the layer comprises breaking the placement rod.

5. The method of claim 3, wherein resilient members secure to the first or second layer, the resilient members comprising nitinol wires.

6. The method of claim 5, wherein anchoring the layers with respect to ischemic tissue comprises urging hooked portions secured to the nitinol wires into at least one of the ischemic tissue and tissue adjacent the ischemic tissue.

7. The method of claim 1, wherein anchoring the layers with respect to the ischemic tissue comprises engaging the layers with a fastener extending through at least one of the ischemic tissue and tissue adjacent the ischemic tissue.

8. The method of claim 1, further comprising injecting a filler between the first or second layer and the ischemic tissue.

9. The method of claim 8, wherein the filler comprises memory foam.

10. The method of claim 1, further comprising interlocking tabs formed on the first layer with tabs formed on the second layer.

11. The method of claim 1, wherein the shape memory material is a shape memory polymer.

12. The method of claim 1, wherein the shape memory material is a shape memory alloy.

13. A method for supporting ischemic tissue in a ventricle, the method comprising:
   overlaying and covering the ischemic tissue with a removable inflatable member having a proximate end and a distal end by placing the inflatable member proximate to the ischemic tissue and inflating the inflatable member in contact with the tissue adjacent to the ischemic tissue;
   inserting a tube through a channel in the inflatable member and beyond the distal end of the inflatable member;
   positioning the tube near the ischemic tissue; and
   injecting a filler material through the tube and into a distended volume between the inflatable member and the ischemic tissue to substantially occupy the distended volume of the ischemic area; and
   removing the inflatable member while leaving the filler material adjacent the ischemic tissue.

14. The method of claim 13, wherein the filler material is memory foam.

15. The method of claim 14, wherein the ischemic tissue is within the myocardium of a ventricle and wherein the filler material and inflatable member are positioned within the ventricle.

16. The method of claim 13, further comprising anchoring the filler material to at least one of the ischemic tissue and tissue adjacent the ischemic tissue.

17. The method of claim 16, wherein anchoring the filler material to at least one of the ischemic tissue and tissue adjacent the ischemic tissue comprises engaging a fastener with the filler material, the fastener penetrating at least one of the ischemic tissue and tissue adjacent the ischemic tissue.

18. The method of claim 13, wherein removing the inflatable member while leaving the filler material adjacent the ischemic tissue comprises deflating the inflatable member.

19. The method of claim 13, further comprising curing the filler material.

20. A method for supporting ischemic tissue in a ventricle, the method comprising:
   positioning a scaffold adjacent the ischemic tissue in the ventricle, the scaffold including at least two layers of biocompatible shape memory material;
   the at least two layers of biocompatible shape memory material positioned adjacent to one another so that a first layer has at least one edge that interlocks with at least one edge of a second layer to form one substantially continuous layer, where the at least one edge of the first layer that interlocks with the second layer and the at least one edge of the second layer that interlocks with the first layer both extend from an apex of the substantially continuous layer to a proximal end of the substantially continuous layer;
   overlaying and covering the ischemic tissue with the substantially continuous layer by expanding the scaffold into a deployed configuration, wherein the substantially continuous layer is placed over the ischemic tissue; and
   anchoring the substantially continuous layer with respect to the ischemic tissue, the anchoring comprising:
   penetrating the substantially continuous layer and ischemic tissue or tissue adjacent to the ischemic tissue with an anchor comprising a coupling portion and a head,
   and after penetrating the substantially continuous layer and ischemic tissue or tissue adjacent to the ischemic tissue, securing the coupling portion to a second head.

21. The method of claim 20, wherein the layer approximately conforms to and overlays walls of the ventricle.

22. The method of claim 21, wherein in the deployed configuration the scaffold forms a cupped shape having a most distal portion thereof near a most distal portion of the ventricle.

23. The method of claim 22, wherein the most distal portion of the scaffold overlays the most distal portion of the ventricle.

24. The method of claim 21, wherein the shape memory material is a shape memory polymer.

25. The method of claim 21, wherein the shape memory material is a shape memory alloy.

26. The method of claim 21, wherein the shape memory material is a multilayer body of shape memory material.

27. The method of claim 20, wherein overlaying and covering the ischemic tissue with the layer comprises urging a placement rod and layer outwardly from a catheter such that the layer is enabled to expand.

28. The method of claim 20, wherein scaffold includes resilient members secured to the layer, the resilient members comprising nitinol wires.

29. The method of claim 28, wherein anchoring the layer with respect to ischemic tissue comprises urging hooked portions secured to the nitinol wires into at least one of the ischemic tissue and tissue adjacent the ischemic tissue.

30. The method of claim 20, wherein anchoring the layer with respect to the ischemic tissue comprises engaging the layer with a fastener extending through at least one of the ischemic tissue and tissue adjacent the ischemic tissue.

31. The method of claim 20, further comprising penetrating the layer with a tube and injecting a filler through the tube and between the layer and the ischemic tissue.

\* \* \* \* \*